United States Patent
Rao

(10) Patent No.: US 9,072,891 B1
(45) Date of Patent: Jul. 7, 2015

(54) WEARABLE MEDICAL DEVICE

(71) Applicant: Dantam K. Rao, Niskayuna, NY (US)

(72) Inventor: Dantam K. Rao, Niskayuna, NY (US)

( * ) Notice: Subject to any disclaimer, the term of this patent is extended or adjusted under 35 U.S.C. 154(b) by 81 days.

(21) Appl. No.: 13/909,197

(22) Filed: Jun. 4, 2013

(51) Int. Cl.
*A61N 2/00* (2006.01)
*A61N 2/06* (2006.01)
*A61N 2/02* (2006.01)
*H01F 3/14* (2006.01)

(52) U.S. Cl.
CPC .. *A61N 2/06* (2013.01); *A61N 2/02* (2013.01); *H01F 3/14* (2013.01)

(58) Field of Classification Search
CPC ......... A61N 2/00; A61N 2/002; A61N 2/004; A61N 2/006; A61N 2/008; A61N 2/02; A61N 2/06; A61N 2/12; A61N 1/04; A61N 1/0404; A61N 1/0424; A61N 1/0452; A61N 1/0456; A61N 1/0472; A61N 1/18; A61N 1/22; A61N 1/32; A61N 1/321; A61N 1/36014; H01F 3/00; H01F 3/02; H01F 3/04; H01F 3/06; H01F 3/08; H01F 3/12; H01F 3/14; H01F 17/04; H01F 17/06; H01F 17/062; H01F 5/00; H01F 6/00; H01F 6/06; H01F 1/375; H01F 3/10; H01F 2003/103; H01F 7/06; H01F 7/066; H01F 7/08; H01F 2007/085; H01F 17/0033; H01F 27/24; H01F 27/26; H01F 27/263; H01F 27/28; H01F 27/2895
USPC ......... 600/9–15; 607/2, 39–41, 45, 46, 61, 72
See application file for complete search history.

(56) References Cited

U.S. PATENT DOCUMENTS

| | | | |
|---|---|---|---|
| 5,078,674 A | 1/1992 | Cadwell | |
| 5,224,922 A * | 7/1993 | Kurtz | 600/13 |
| 5,725,471 A | 3/1998 | Davey et al. | |
| 6,086,525 A | 7/2000 | Davey et al. | |
| 6,500,110 B1 | 12/2002 | Davey et al. | |
| 6,527,695 B1 | 3/2003 | Davey et al. | |
| 6,885,895 B1 | 4/2005 | Whitehurst et al. | |
| 6,971,393 B1 | 12/2005 | Mamo et al. | |
| 7,104,947 B2 | 9/2006 | Riehl et al. | |
| 7,320,664 B2 | 1/2008 | Riehl et al. | |
| 7,337,005 B2 | 2/2008 | Kim et al. | |
| 7,660,631 B2 | 2/2010 | Whitehurst et al. | |
| 7,824,324 B2 | 11/2010 | Riehl et al. | |
| 7,865,243 B1 | 1/2011 | Whitehurst et al. | |
| 7,963,903 B2 | 6/2011 | Ghiron et al. | |
| 2001/0026205 A1 * | 10/2001 | Paris et al. | 335/297 |
| 2002/0097125 A1 | 7/2002 | Davey et al. | |
| 2007/0027355 A1 * | 2/2007 | Riehl et al. | 600/13 |
| 2010/0331604 A1 * | 12/2010 | Okamoto et al. | 600/13 |
| 2011/0015464 A1 | 1/2011 | Riehl et al. | |
| 2011/0125203 A1 | 5/2011 | Simon et al. | |
| 2012/0101326 A1 | 4/2012 | Simon et al. | |
| 2012/0302821 A1 | 11/2012 | Burnett | |

* cited by examiner

Primary Examiner — Charles A Marmor, II
Assistant Examiner — Carrie R Dorna

(57) ABSTRACT

This disclosure describes a Wearable Magnetic Stimulator to treat a variety of disorders. The device comprises a wearable stimulator head and a wearable stimulator controller. The patient wears the stimulator head over skin close to the target nerves and carries the wearable controller in his clothing. The wearable head comprises a small gapped cut-core energized by coil windings. The head operates on the principle that its small gap injects fringe flux into target nerves, which induces ionic currents that cure disorders. Small gapped cores require significantly smaller current than large gapped cores. This greatly reduces the size and weight of the head and controller. The wearable controller, such as a cell phone, comprises pulse generator hardware and software from internet. The wearable stimulator can be used to treat several disorders such as migraine headache, arthritis, incontinence, depression, erectile dysfunction etc.

11 Claims, 11 Drawing Sheets

100 Wearable Stimulator Head

200 Wearable Stimulator Controller

215 Internet

WEARABLE MEDICAL DEVICE

FIELD OF THE INVENTION

This invention relates to magnetic stimulators that inject magnetic fields into target nerves, blood vessels or muscles to treat disorders.

BACKGROUND OF INVENTION

Non-drug therapies can be classified as invasive and non-invasive procedures. Non-invasive procedures do not employ surgery and have several attractive features over invasive surgical procedures. They do not cause damage to biological tissues, do not result in skin injury, do not cause bleeding, blood clotting, infection or internal organ injury and hence are less risky. They do not require drugs or local anesthesia, so are painless. They do not require skilled surgeons, do not need extended stay in hospitals or long recuperative time in bed and so are less expensive. In view of the lower risk, pain and cost benefits, patients are increasingly favoring non-invasive treatments over surgical procedures.

A non-invasive procedure of particular interest is pulsed magnetic stimulators that inject magnetic fields into target nerves, blood vessels or tissues, inducing currents that release neurotransmitters to treat various disorders. The ionic current pulses can also synthesize curative molecules in tissues. This operating mechanism is similar to ECT or defibrillators, but they differ in that they inject magnetic fields instead of current. Changes in magnetic fields induce currents so have the same ultimate effect. Prior art has developed several stimulators but none of them are wearable as discussed below.

FIG. 5 illustrate a few prior-art magnetic stimulator heads. FIG. 5A shows a prior art "Neocon chair" 42 (developed by Neotonus Inc. GA) as described in U.S. Pat. Nos. 6,086,525 and 6,500,110 and is used to treat incontinence. The patient 41 sits in a chair 42 with her pelvic bottom 50 resting on a chair 43 containing a stimulator head 44 that produces magnetic field 46, which stimulates pelvic floor nerves 48. The stimulator head 44 is a large-gapped iron-cored electromagnet as described in U.S. Pat. Nos. 5,725,471, 6,086,525 and U.S Pat. Pub. 20020097125, is too heavy so is non-wearable. Per U.S. Pat. Pub. 20110125203, the stimulator controller delivers ~5.000 amps, so is very large, heavy and non-wearable. Thus, the Neocon chair 42, the magnetic stimulator head 44 and the stimulator controller are too heavy and non-portable so are non-wearable.

FIG. 5B, inset (a) shows another prior-art stimulator head 52 (developed by Neotonus Inc, GA) that is used to treat knee muscle problems as described in U.S. Pat. No. 5,725,471. Known as Neotone™, the stimulator head 52 also employs a large-gapped C-core; a technician holds it close to the knee 54 spaced by an air gap 58. The head radiates magnetic fields 56, which induce currents in blood vessels to start the healing process. Both the large-gapped stimulator head 52 and its controller are too heavy and hence non-wearable.

FIG. 5B, inset (b) shows an alternative air-cored stimulator head 62 as described in U.S. Pat. Appln. 20120302821 that is used to treat ankle muscles. This stimulator head 62 is secured to the knee 54 by a wrap 64 to stimulate tibial nerve 57. Although this head appears to be wearable, it demands very large currents that could overheat the knee 54 and cause skin burns.

FIG. 5C shows another air-cored stimulator head 72 atop the wrist 390 to treat wrist injuries, as in U.S. Pat. No. 5,078, 674. The stimulator head 72 is a petal shaped, near-circular coil with sharp corner 76 and rests on the skin 395 of the patient. The sharp corners cause flux concentration which results in higher neuron depolarization. However, the stimulator head 72 atop the hand is not wearable. The associated stimulator controller generates thousands of amperes so is too large and heavy to be worn by a patient, and hence is non-wearable.

FIG. 5D shows another prior art electrical stimulator head Gammacore® 82 (developed by Electrocore, NY) described in U.S. Pat. Appln. 20120101326 and is used to treat migraine headaches and. It is a hand-held device comprising iron-cored toroids with two electrodes 87, 88 at the ends. The patient 90 holds the stimulator head 82 in his hands 89 and presses it against the vagus nerve 84 which is located in the left side at bottom of the neck. This manufacturer also produces another electrical stimulator head Alphacore® described in U.S. Pat. Appln. 20110125203 to treat incontinence. Both Alphacore® and Gammacore® are handheld electrical stimulators (not magnetic stimulators) as they apply currents to electrodes near the nerves. Even though they are portable and handheld, they are very large, heavy and require hands to hold, so are non-wearable.

Prior-art has also developed several air-cored magnetic stimulator heads and used them to treat Spinal Cord Injury (SCI). The patient positions them at upper, middle or lower portions of spinal cord such as C3 to C5. However, they are also very large and require a heavy stimulator controller, so are non-wearable. V. Lin in Spinal Cord Medicine: Principles and Practice, pp. 749-755, 2003 published a comprehensive survey of such air-cored stimulators. Per this survey, air-cored stimulators are as large as 90 to 120 mm so are non-wearable. They require heavy and large pulse generators with ~5000-amp capacity. U.S. Pat. Appln. 201220302821 describes a wearable air-core stimulator head that is built into underwear. However, it requires a stimulator controller that is too large and heavy, so the system is non-wearable. Thus all these prior art stimulators employed large-gapped cores, they require large and heavy controllers so are non-wearable.

SUMMARY OF THE INVENTION

One major object is to allow a patient to self-treat disorders without invasive surgery. Another object is to present a medical device that is wearable. Another object is to present a wearable medical device that can treat a variety of diseases such as erectile dysfunction, depression, migraine headache, incontinence, knee injury, etc. Another object is to present a wearable device that can stimulate deep nerves in the brain. Another object is to present a wearable medical device that is significantly smaller and lighter. Another object is to present a wearable medical device that reduces the treatment time and cost. Another object is to present a wearable medical device that is economical to manufacture. Another object is to present a wearable medical device that uses least number of parts and processes. Another object is to present a wearable medical device that is cooled by natural convection. Another object is to present a wearable medical device that does not need a helmet or skullcap. These and other objects can be understood by a person skilled in the art on perusal of the detailed description of the invention.

The disclosed wearable medical device comprises a wearable stimulator head and a wearable stimulator controller. Each is enclosed in separate but interconnected housings. Both are wearable, compact, lightweight and consume low power. The wearable head comprises a small gapped core with coil windings. The patient wraps the wearable head around the limb that contains target nerves. The wearable controller is a current pulse generator with control electronics. The patient carries the wearable controller in his cloth pockets or a belt-clip. An electric cable connects the wearable controller to the wearable head.

The wearable medical device operates as follows. The wearable controller supplies a current pulse train to the coil windings in the wearable head. A small gap in the cut-core injects fringe flux into target nerves. Changes in the fringe flux induce currents in the target nerves. These ionic currents release neurotransmitters and the resulting electrochemical message transmitted into the nerve endings causes chemical reactions that cure disorders.

The wearable head is a small gapped core excited by a coil winding. It is contained in an insulative and protective housing. The cut-core surrounds the limb containing the target nerves. The cut-core may be a toroid made of flexible soft magnetic material. The core has thin-walled section and made from soft magnetic materials of high permeability such as silicon steel strips, amorphous steel strips, nanocrystalline etc. The coil winding is made of Litz wire to reduce AC losses. A female jack termination of the coil and a matching male jack termination in an electric cable connect it to the wearable controller. Thus, the wearable head is relatively small and lightweight compared to prior art stimulators.

The wearable controller is a programmable pulse generator that can drive the wearable head. An electrical cable to the wearable head connects it. It contains pulse generator and control electronics, viz. power source, pulse generator, controller, display, control keys, software etc. A cell phone with software downloaded from internet can be used as a wearable controller or its output fed into the controller. The wearable controller typically operates on an internal power source such as a 9-volt rechargeable battery. The patient or a specialist programs inputs key parameters into the software.

The wearable head treats disorders as follows. The patient downloads a stimulation app (customized software to suit specific illness) from the internet into the cell phone controller. He mounts the wearable head over the skin in such a way that the small gap injects fringe flux into the target nerve. He connects the wearable head to the cell phone/controller via a cable. He carries the cell phone/controller in the clothing, e.g., in a pocket or waist-belt etc. He starts the downloaded stimulation app. This downloaded app converts the cell phone/controller into a programmed pulse generator. The pulse generator transmits current pulses to the stimulator, which injects fringe flux into target nerves. Changes in fringe flux induce an electrical message train in the target nerves that goes into the muscles and blood vessels to heal them.

The head can be used to treat a variety of disorders. For example, a 9" elliptical wearable head around the face can treat depression. A 2" diameter stimulator head can treat erectile dysfunction over the penis. A 4" diameter head around the neck can treat migraine headache. The head of various sizes can be worn over the patient's neck, abdomen, pelvis, ankle or any other limb containing target nerves such as parasympathetic nerves, sympathetic nerves, spinal or cranial nerves, tibial nerves, brain neurons etc or nerves that control skeletal muscle, endocrine glands, or organs of the digestive system to treat several disorders.

The patient wears the head over the injured limb such as head, neck, abdomen, pelvis, knee, ankle, penis etc. He can use it discretely to treat a variety of medical disorders, without disturbing the daily routine. He has unprecedented degree of control over every aspect of the treatment. He can set his own treatment time and duration. He may be at home, at work, relaxing or sleeping when the stimulator works in the background silently. He can carry the treatment in any posture, such as sitting, standing, walking, or jogging. He can adjust the strength of stimulation or its frequency for optimal therapy. He is freed from making trips to medical facility to get similar treatment. He has the option to treat himself or seek trained medical assistance. The cost of treatment will be less, as he need not rely on expensive medical insurance, facilities or professionals.

DESCRIPTION OF THE EXEMPLARY EMBODIMENTS

The wearable medical device comprises a wearable stimulator head 100 and a wearable stimulator controller 200, both electrically connected by a cable 110. The wearable device employs Faraday's principle that when current pulses drive an electromagnet, its small gap injects fringe flux that induces ionic currents in a target nerve to cure diseases. A patient wears the head with a small gapped wound core around an affected limb containing a target nerve. The patient also carries a cell-phone sized stimulator controller in the clothing. The controller generates a train of current pulses while the small gap injects fringe fields into target nerves. The fringe fields induce ionic currents, which form a curative electrical message that travels along the nerve to its endings. The nerve endings release electro-chemicals that react with muscles and blood vessels resulting in therapy. The term "core" herein is synonymous to the wearable stimulator head.

Figure 1A:
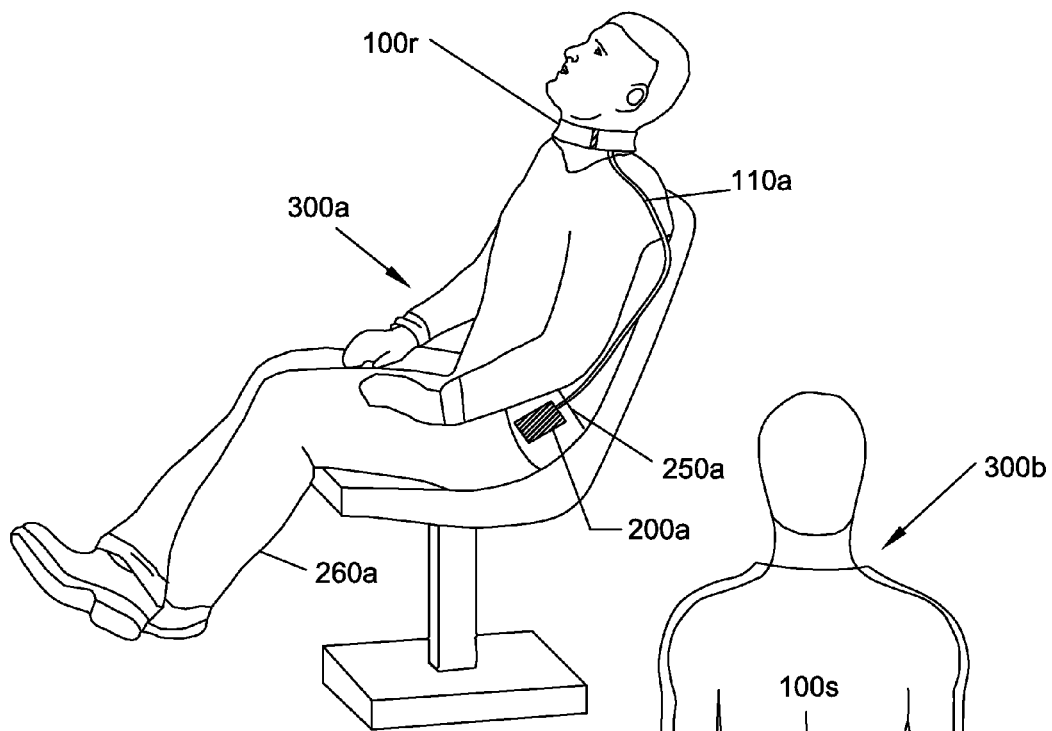
FIG. 1 show typical ways of wearing the disclosed magnetic stimulator, with FIG. 1A showing it worn around the neck and FIG. 1B showing it worn around the waist.
Figure 1B:
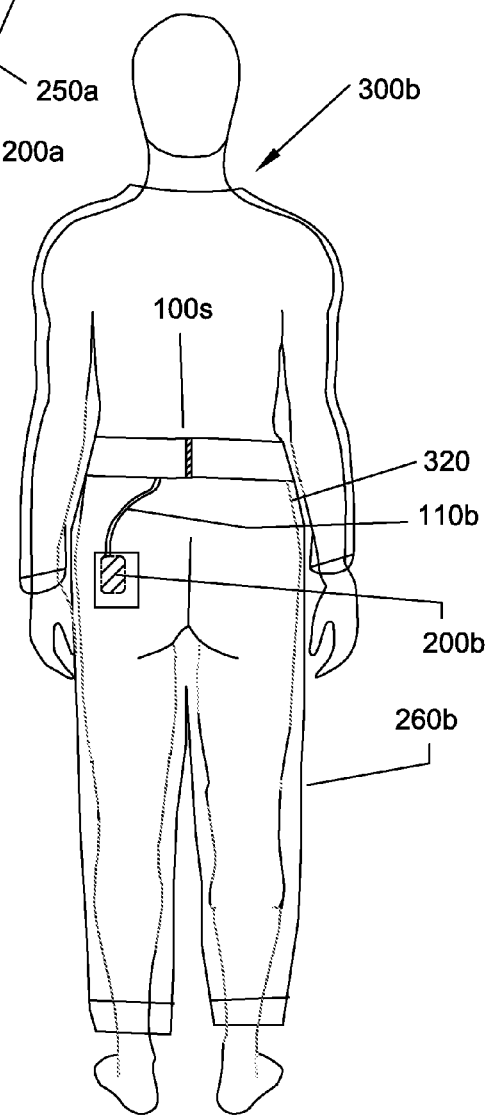

The patient can carry the wearable medical device in any posture. For example, FIG. 1A shows a patient in sitting position while FIG. 1B shows a patient in standing position. FIG. 1A shows the sitting patient 300a wearing the small-gapped head 100r around neck close to the vagal nerve and carries the stimulator controller 200a inside the pocket 250a of trousers 260a. A cable 110a electrically connects the wearable head 100r to the stimulator controller 200a. Alternatively FIG. 1B shows a standing patient 300b wearing the small-gapped head 100s over spinal nerves in lower back 320 and carries the stimulator controller 200b inside trouser pockets 260b. A cable 110b connects the wearable head 100s to the wearable controller 200b. A person skilled in the art can develop other styles of wearing the stimulator without altering the scope of the invention.

Figure 2A:
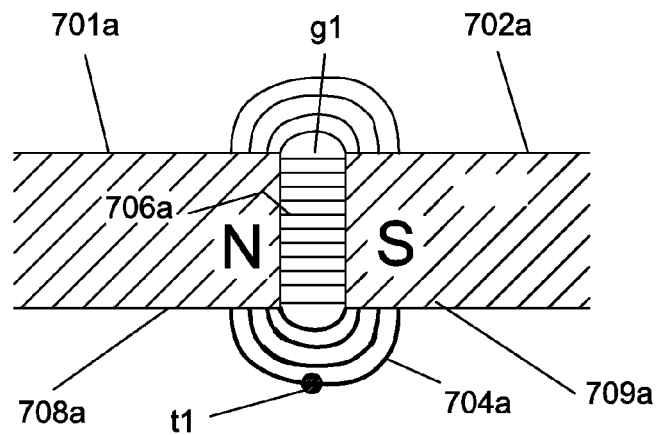
FIG. 2 show the basic operating mechanism of the wearable magnetic stimulator, with FIG. 2A showing how a small gap generates fringe flux and FIG. 2B showing how fringe flux is injected into a target nerve.

FIG. 2A illustrates the basic mechanism of the wearable magnetic stimulator. When an iron cored electromagnet 701a, 702a has a small air gap g1, the faces forming the gap have opposite polarity. The face that spills out flux becomes a North Pole N while opposite surface that receives flux becomes a South Pole S. Each Pole has a pole face that is perpendicular to the gap and two reluctance faces that are parallel to the gap. Most of the flux, termed main flux 706a flows from North Pole face to South Pole face through the small air gap g1. The remainder flux 704a, radiating from North Pole reluctance face 708a and received by South Pole reluctance face 709a, is termed fringe flux. (Fringe flux that flows across outer reluctance faces is not shown for clarity) The disclosed invention injects this fringe flux 704a into target nerves t1 that is normal to the plane of flux to cure disorders. (In contrast, the prior-art used a large gapped core where the main flux that travels from one pole face to other pole face). The target nerves are normal to the fringe flux. It operates on Faraday principle that changing magnetic fields induce electric fields in a conductive medium. Per Faraday law, changing fringe flux 704a induces currents in the target nerve t1. The stimulator software programs these induced currents, creating a therapeutic electrical message that travels through the target nerve t1, which cures the disorder controlled by it.

Figure 2B:
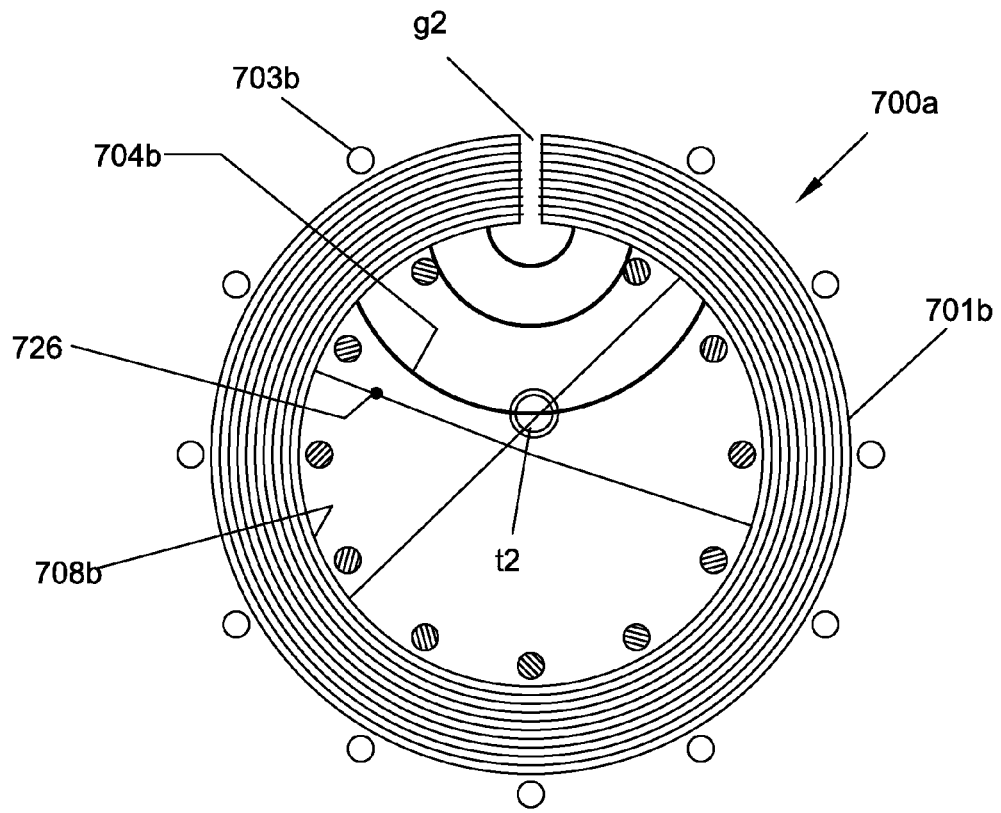

FIG. 2B shows a conceptual wearable head 700a that wraps around a limb 726. The limb 726 (such as arm, leg, neck, head etc.) is modeled as a circular section 708b and carries target nerve t2 that run perpendicular to the plane the paper. The wearable head 700a is similar to a bracelet; it is a closed loop core 701b with a small air-gap g2. A coil winding 703b energizes the small gap. The patient wears the head 700a such that its inner periphery 708b surrounds a limb 726. The trapped fringe flux 704b flows within inner periphery 708b from one side of the gap to the other side. (The figure does not show the main flux and fringe flux over outer periphery for clarity.) The core 701b and its small air gap g2 are oriented such that they apply fringe flux 704b into the target nerve t2. The controller applies a current pulse train to the coil 703b which results in electrical message in the nerves. Changes in the fringe flux 704b induce current in the target nerves t2 per Faraday law. When this fringe flux is normal to nerve fibers, changing fields induce maximal voltage. Then the wearable head needs minimal coil current to produce maximal ionic current in the target nerves. The nerve endings transmit this message to the muscles or blood vessels controlled by it, resulting in therapeutic treatment.

Figure 3A:
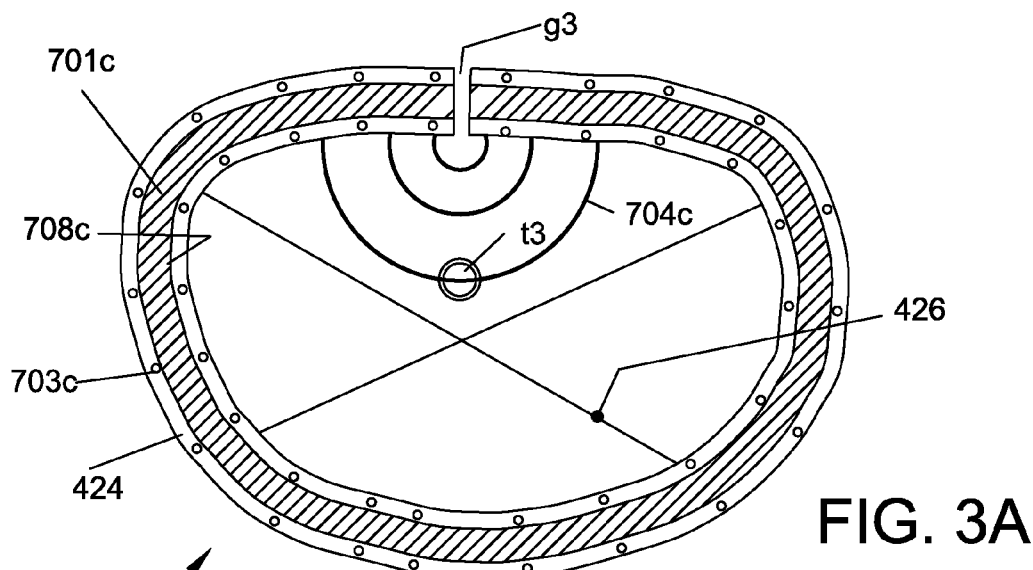
FIG. 3 show the basic components of a wearable magnetic stimulator, with FIG. 3A showing the wearable head with a small air gap injecting fringe flux into a target and FIG. 3B showing a cell phone used as a wearable controller.
Figure 3B:
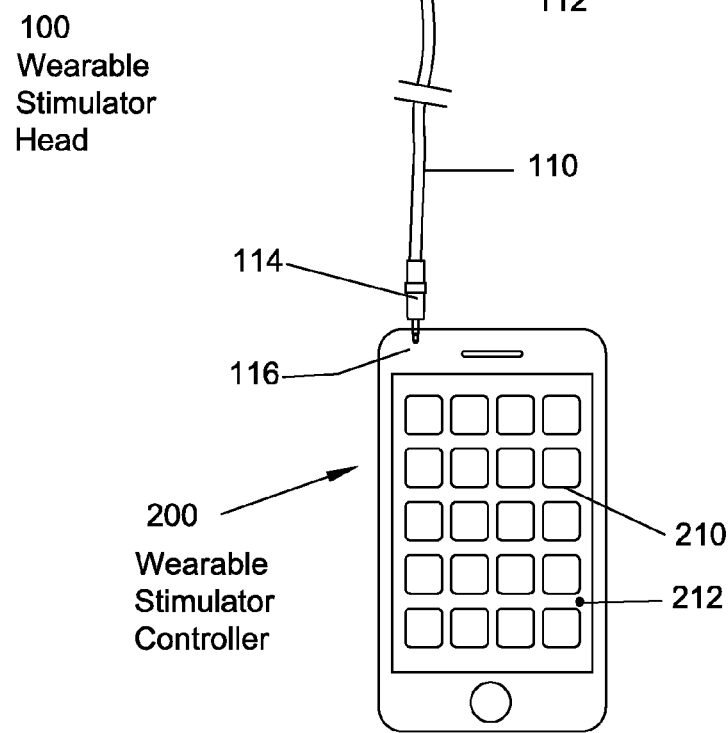

FIG. 3A show the wearable stimulator head 100 while FIG. 3B shows a wearable stimulator controller 200, both connected by a cable 110. The wearable head 100 comprises a small gapped core 701c having a small air gap g3 and a coil winding 703c, both enclosed in a protective housing 424. The small gapped core 701c surrounds a limb 426 that contains target nerves t3, which flow normal to the plane of paper.

The wearable head 100 in FIG. 3 stimulates the target nerves as follows. The small gap in the wearable head produces trapped fringe flux lines 704c that close on inner reluctance faces 708c. The air gap g3 is oriented such that it injects fringe flux lines 704c into the target nerve t3. Per Faraday's law, changes in the fringe flux 704c induce current in the target nerves t3. A properly sized train of current pulses in the coil therefore causes an electrical message in the nerves t3. The message travels to the nerve endings, which cause related muscular tissue and blood vessels to respond resulting in beneficial treatment of the disorder.

The small gap g3 is smaller than flux path through core or the width of pole faces. This small gap g3 ranges 0.004" to 0.020". In contrast, prior-art employed a large-gap ranging 3" to 8". The small gap in the present disclosure is two to three orders smaller than the large gapped core used in prior-art. The present disclosure hence requires one-hundredth to one-thousands less amp turns than prior art. Such reduction in power sharply drastically reduces the size and weight of the stimulator head and the stimulator controller, making them so light and small to be wearable.

The small-gapped core comprises thin electrical steel strip with high permeability, high saturation, and low core losses and is bendable. Its thickness can range from 0.025 mm (0.001") to 0.2 mm (0.008"). The eddy loss increases with frequency squared. So, when carrying fluxes pulsed at ~5 kHz, the core might overheat. Example materials are woven laminated steels, high permeability nickel-iron alloys, Metglas, silicon steel or magnetic stainless steel, etc. Low-loss materials such as Metglas, nanocrystalline or nickel alloys can produce less waste heat. A thin insulative coating on a steel strip can reduce interlaminar eddy current loss. The core 701c is preferably of narrow rectangle-section as it stimulates nerve fibers along entire width, producing more ionic currents. In alternate round-sectioned core, flux from the steel surface that grazes the limb only will stimulate the nerves; flux from other non-grazing areas does not link the nerves so does not stimulate them. So round sectioned cores are not as effective as rectangle-sectioned cores. FIG. 4 show a few example embodiments of the small-gapped core.

Figure 4A:
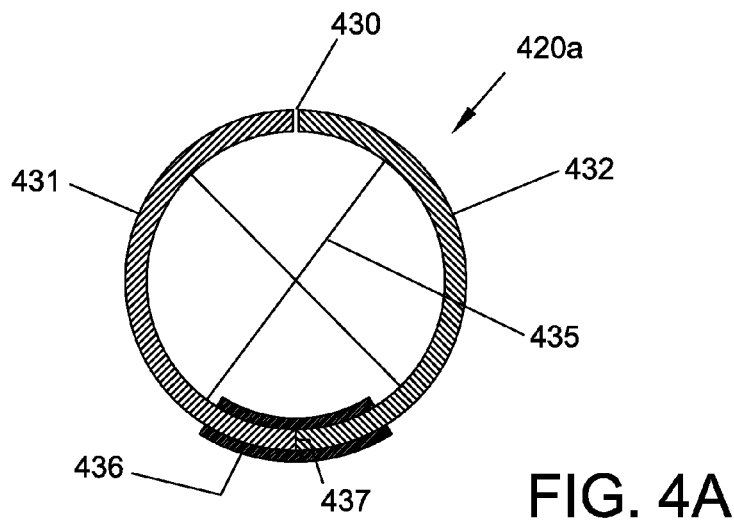
FIG. 4 show various embodiments of the wearable magnetic stimulator head, with FIG. 4A showing two half-cores jointed by a sleeve, FIG. 4B showing a cut-toroid made by winding a steel strip around a preform, FIG. 4C showing a steel belt section made of fine steel wire, FIG. 4D showing a rope section made of fine steel wire.

FIG. 4A shows one embodiment 420a of the small-gapped core. Two segmental cores 431, 432, joined at one end 437 by a sleeve 436 and separated by a small gap 430 at the other end form the core. The segmental cores 431, 432 is a thin steel strip that may or may not be laminated. A laminated version can be made as follows. One winds a resin-coated steel strip over a large spool to form a hoop of desired thickness and spot-welds the ends. After curing the adhesive, one cuts the ring at one place, unwinds and flattens to yield a long laminated belt. If needed, one may anneal the belt to restore magnetic properties. A single or double acid etching cleans the cut edges. One then cuts this belt to required length and bend it around a preform that simulates limb 435 to form segmented cores 431, 432. One then joints both segmented cores by a sleeve 436 so that this end 437 has no magnetic gap while the other end 430 has a finite but small gap. A person skilled in the art can configure the sleeve joint in several ways without affecting the invention.

Figure 4B:
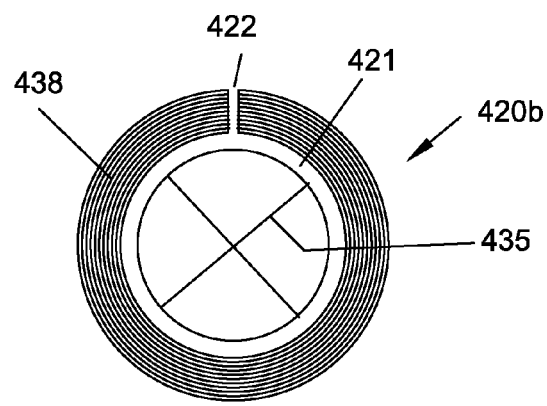

FIG. 4B shows an alternative embodiment 420b of the small gap core. It is made of steel strip 438 coated with flexible resin and wound around a perform 421 that mimics a limb 435 (containing target nerves) and cured to form a toroid. The toroid may be stress relieved to restore magnetic properties. A thin diamond saw makes a radial cut 422 to form the small gap. One cleans the cut faces by double etching to dissolve embedded iron particles. The gap could be of uniform or nonuniform thickness. Arbitrarily different ways can be used to configure it as known in the art without affecting the invention.

Figure 4C:
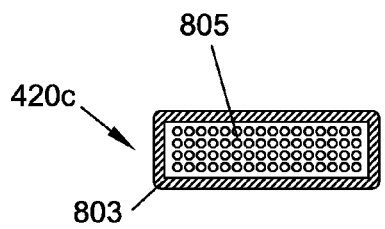

FIG. 4C shows an alternative section 420c of the small gap core. It comprises a tubing 803 of rectangular section, packed with fine steel wires 805. The wires 805 can be made of low carbon steel; they can be bundled, twisted and annealed. The diameter of wires 805 ranges 0.001 to 0.008 inches to minimize eddy current losses and to increase flexibility. On then bends the steel belt into circular loop around a pre-form that mimics a limb section. After bending, one can re-anneal it to restore magnetic properties. A rectangular section is more flexible around its easy axis of bending. The saturation flux density of steel wires is relatively high, but its permeability is smaller than electrical steels.

Figure 4D:
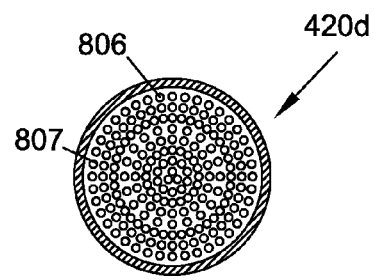

FIG. 4D shows an alternative section 420d of the small gapped core. This core comprises soft steel wires 807 packed in a round plastic tubing 806. The round shape is useful where flexibility in two directions is required. But, since the round sectioned core is not as effective as rectangular sectioned core this embodiment has limited usage.

Alternately, the core may be multi-gapped, comprising wound toroid split into two or more arcs, which are jointed and assembled around limb. Alternately, one can perforate the steel strip 438 to increase flexibility. Alternately, one can build a core by laying rectangular strips in a brick-like fashion and molding it. Alternately, the core ends could be coplanar to inject fringe flux in the longitudinal plane of the limb. The faces that form the gap could be either parallel to deliver uniform fringe flux or tapered to deliver focused fringe flux.

Generally, the coil winding 703c comprises Litz wire as it will reduce skin and proximity losses at high frequencies. The number of turns, diameter of the Litz wire, strands, twist angle etc. are chosen to carry high frequency currents. The Litz coil and the small gapped core can be potted in flexible compound such as silicone, which also manifests as a protective housing. The ends of the winding 703c are connected to a female audiojack that is built into the stimulator. A male audiojack terminal 112 of cable 110 electrically connects to the female jack or in the wearable head (FIG. 3A). A cable 110 with male plugs 112, 114 at the ends connects the wearable head 100 to the wearable controller 200. The male 112 of the cable 110 plugs into the female in the wearable head 100 while the male 114 of the cable 110 plugs into the female 116 in the wearable controller 200. The plug could be a 2.5 or 3.5 mm audio jack. Alternately, the audiojack terminals could be replaced by USB ports. A person skilled in the art can conceive of arbitrarily other styles of wearable head 100 with cut-core such as straps, bracelets, split rings, castings, belts, wraps, tapes etc without altering the scope of the invention.

FIG. 3B shows one embodiment of a wearable stimulation controller 200, viz. a cell phone controller. The wearable controller contains a power source, and pulse generator and control software. It generally utilizes the hardware inside the cell phone. One can augment the cell phone with a separately housed pulse generator to deliver more power into the wearable head if needed. The cell phone controller 200 comprises a programmable pulse generator, a computer storing a treatment app and a user interface. It is normally carried by a patient via belt clips or in the pockets of trousers etc. The cell phone controller 200 drives currents in the coil windings. It uses stimulation software, viz., a collection of treatment app 220 that is stored in servers connected to the internet. Each app 220 is software that generates an electrical message tailored to a specific target nerve to treat a specific disorder. The app contains a digitally programmed custom waveform. The user can change the strength, duration and shape of the waveform to suit a specific target nerve. The app is a software that contains an input section, a process section and an output section. The input section receives the programmable parameters from the user interface. The process section uses input parameters to prepare a control signal. The output section converts the control signal into coil currents. The wearable head converts coil currents into an electrical message that stimulates target nerves.

A therapy session may comprise several steps, e.g., mounting the head for minimizing coil current, trial programming to locate target peripheral nerves, testing and setting stimulation limits, final programming, setting duration and strength of electrical messages etc. The program code is written to fulfill all these needs. As a minimum, the treatment app 220 displays a "Start", "Program", "Test", "Run" and "Stop" icon. The "Start" icon initializes the software to specific conditions. The "Program" icon allows one to set and shape the electrical message parameters. The "Test" icon allows one to test and set the limits of the coil currents to prevent overstimulation. The "Run" icon causes the cell phone to send preprogrammed current pulses into wearable head 100. An electrical message may comprise a burst of 1 to 20 signal pulses at 20 to 1000 μs (1000 to 50000 Hz) interval with several pulse bursts repeated at 0.02 to 1 sec (1 to 50 Hz) over a treatment session. A typical current pulse may be at 5 kHz repeated at 15 Hz for 30 minutes.

The wearable controller 200 operates as follows. To start the treatment, the patient downloads a specific treatment app 220 from internet 215 into a computer 212 inside the cell phone controller 200. The patient programs the cell phone controller 200 using the cell phone display icons 210 to select proper stimulation parameters. Once properly programmed, the injected electrical message travels along the nerve fibers to the nerve endings which interact with connected muscles to cause beneficial magnetic therapy. Some or all of the programming and testing functions can be carried either by the patient himself or by a trained medical professional. The following sections illustrate the use of the wearable medical device to treat typical disorders.

Migraine Headache

Figures 6A, 6B, 6C:
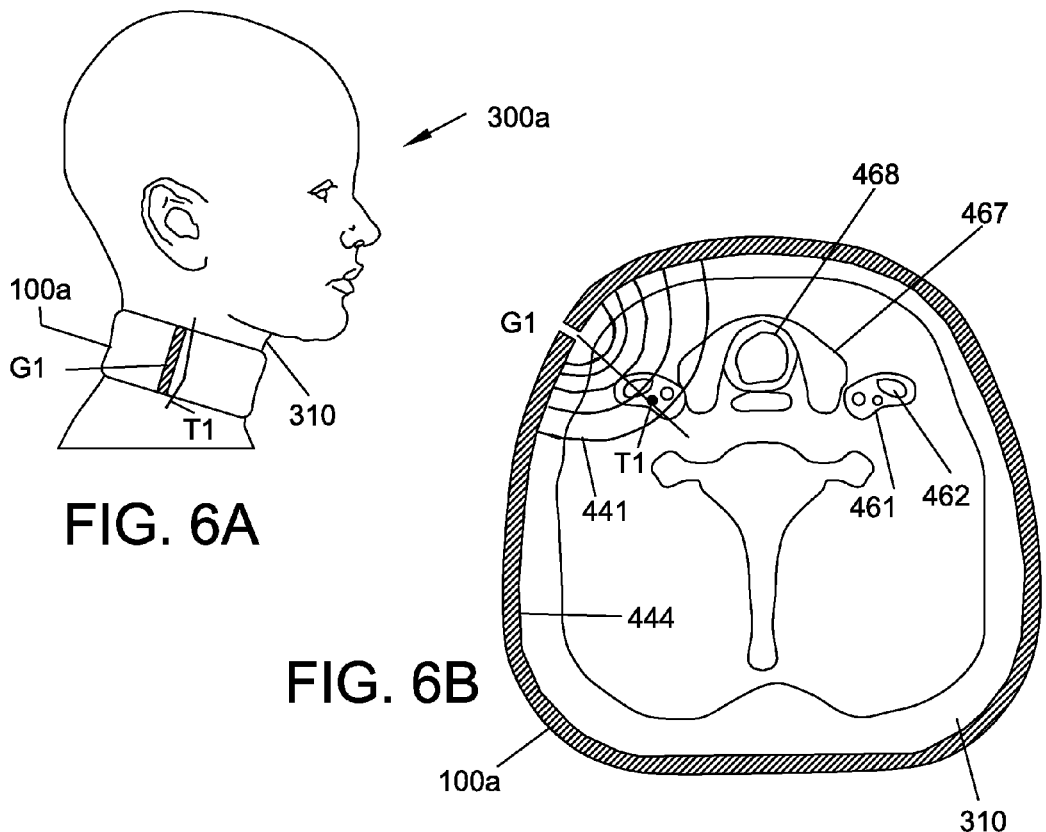
FIG. 6 show a wearable stimulator to treat migraine headache or depression, with FIG. 6A showing the wearable head around patient's neck, FIG. 6B showing it injecting fringe flux into vagus nerve and FIG. 6C showing the variation of electric field along a line joining air gap and target nerve.

More than 28 million people are estimated to suffer from migraine headaches in US. In fact, more people suffer from migraine headaches than diabetes and asthma combined. FIG. 6A shows a wearable head 100a wrapped like a collar around the neck 310 of a patient 300a to stimulate vagal nerve. Such vagal nerve stimulation can be used to treat depression, epilepsy or migraine headache. The therapy works similar to the prior art VNS (Vagal Nerve Stimulator) which injects currents to treat depression or epilepsy. The wearable stimulator 100a injects magnetic fields (instead of currents) which in turn induce currents that serve the same function. The head 100*a* has a cut-core with small gap G1 that emits fringe flux. The air gap G1 is oriented so that the line joining G1 and target T1 is normal to the air gap (FIG. 6B). A cell phone/controller (not shown) applies small current pulses into the coils. The air gap G1 then injects fringe flux 441 into vagus nerve T1. Changing fringe flux 441 induces electric field in the vagus nerve T1 and causes an ionic current pulse. This creates an electrical message that is transmitted from vagus nerve T1 to the brain. These results in neurotransmitters which tend to reduce depression, epilepsy or migraine headache.

FIG. 6B shows a neck 310 surrounded by a stimulation core 100*a*. The coil, cell phone controller and connecting cable that power the stimulator head are not shown for clarity. The vagus nerve T1 is located within the left cartoid sheath 461 that also encloses the jugular vein 462. The figure also shows the thyroid gland 467 and esophagus 468 for reference. The small gap G1 injects fringe flux lines 441 into the vagus nerve as shown. These fringe flux lines 441 close over the inner periphery 444 of the core. They are normal to vagus nerve T1, so induce strongest ionic current. The controller applies currents to the coil of such magnitude that changing fringe flux induces an electric field of more than 100 V/m on the vagus nerve T1 thereby stimulating it leading to curative electrical message.

Finite element analysis is used herein to establish that the wearable stimulator 100*a* can treat disorders such as depression, epilepsy, migration headache etc. The 5 mm (0.187") thick core 100*a* is and a coil with 5000 turns is worn around a 4.5"neck. It has a small air gap G1 as shown in FIG. 6B. A controller applies a 0.1 amp current at 5000 Hz to the coil. FIG. 6B show the small gap G1 emitting fringe flux lines 441. Changing fringe flux lines inject electric field into the target nerve T1. FIG. 6C plots variation of this field along a line that starts from the air gap G1, passes through the vagus nerve T1 and extends up to 2". The target T1 is 1.25" (30 mm) from the air gap G1. This plot 491 shows that around the skin close to gap G1, the electric field is ~100V/m. Since it is known that fields below ~100 V/m do not stimulate, it is clear that the wearable head 100*a* does not cause pain due to nerves within the skin. FIG. 6C also shows the electric field increases as target depth increases. Specifically, it shows that the electric field E1 at the vagus nerve T1 is 135 V/m. Since electric field above 100 V/m is known to stimulate a nerve, it is evident that the wearable head can stimulate the vagus nerve without causing pain in the neck.

Depression

Figure 7A:
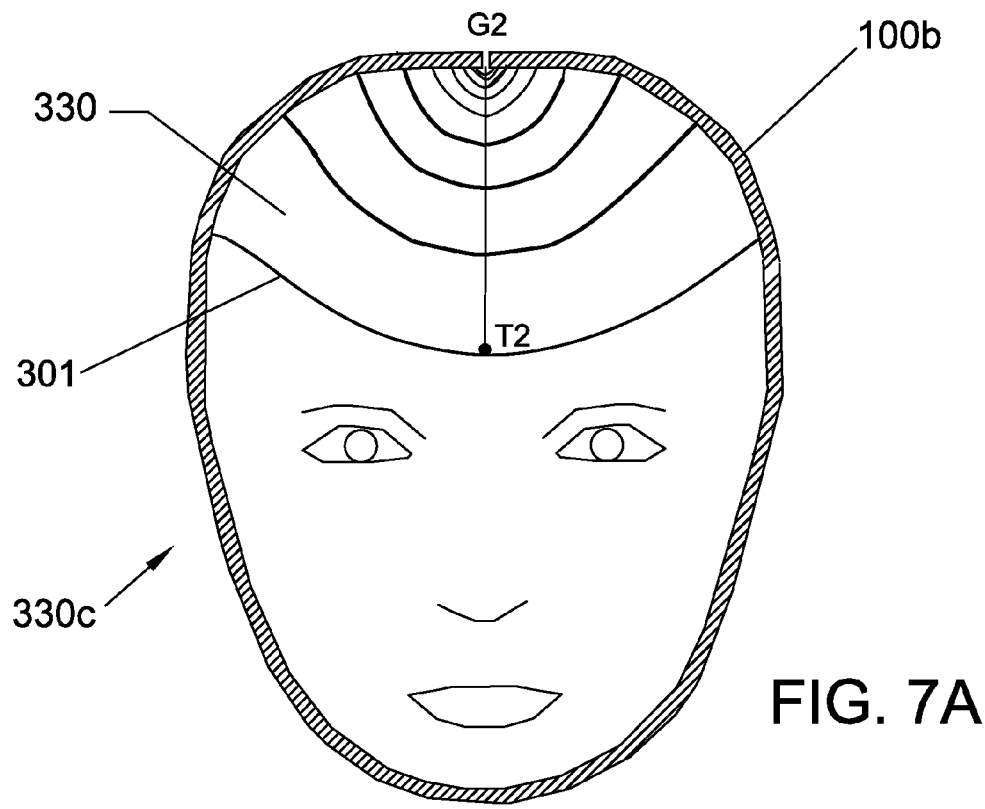
FIG. 7 show a wearable stimulator over scalp to treat depression, with FIG. 7A showing it injecting fringe flux into the target nerves and FIG. 7B showing the electric field along a line joining the small gap and target nerves.

More than 19 million people in U.S. and 340 million worldwide are estimated to suffer from depression. FIG. 7A shows a flexible cut-core 100*b* worn over the head 330*c* of a patient to treat depression by stimulating target neurons at T2 in the brain. For clarity, this figure does not show the coils, the wearable controller or the connecting cable. The target nerves could be at shallow depths (less than 30 mm) to cure depression, or be deep (about 80 mm) to cure Parkinson's disease, depression etc. The wearable head is an electromagnet comprising a cut-core 100*b* with a small gap G2 that is energized by a Litz coil winding. The figure shows the gap G2 located at the crown to stimulate a target T2 down below in the plane of the paper. But the air gap is located at a place closest to the target. For example, to stimulate target nerves located at ~45° CCW from the crown of head, the stimulator is also rotated 45° CCW so that fringe flux lines from the air gap is at the shortest distance. The gap G2 injects fringe flux lines 301 into the target T2. The flux lines are normal to target T2 yielding largest ionic current into the target nerves.

To start the depression treatment, the patient employs the wearable head 100*b* as shown in FIG. 7A. He or his doctor downloads the depression-treatment software from the internet into a wearable controller and connects it to the wearable head 100*b* via a cable. He then enters the treatment parameters into the stimulation software. If needed he can send test signals to establish the range of current needed to stimulate the target without causing pain. The software then causes the stimulation controller to transmit a series of current pulses to the wearable head 100*b*. The airgap within core injects fringe fields 301 into the target T2. Changing fringe fields induce current pulses or electrical messages. The electrical message causes neurotransmitters to be released from presynaptic neurons thereby alleviating symptoms of depression.

Figure 7B:
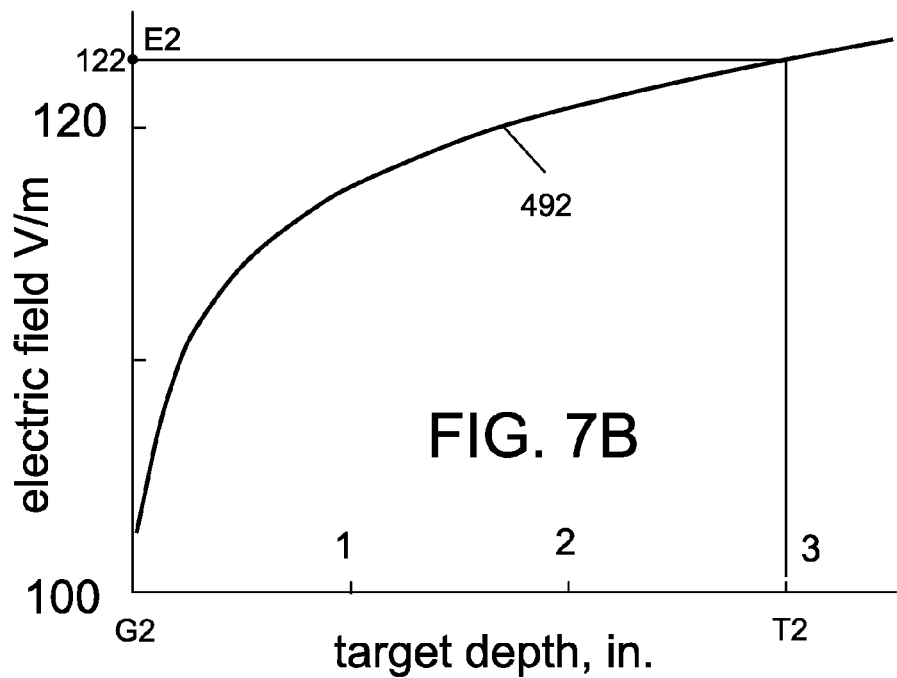

Prior-art TMS stimulators are known to be limited to shallow targets, viz., those at depths less than 1.25" (<30 mm depth). In contrast, the wearable stimulator can stimulate deeper targets (~80 mm depth). To establish that the wearable stimulator can perform deep brain stimulation, a finite element analysis was conducted. FIG. 7A shows a complex shaped human head with a flat top, an oval face and a round chin. The head is 5.5" (140 mm) between ears and 9" (230 mm) from crown to chin. The target nerves T2 is at a depth of 3" (80 mm) from the gap G2. The wearable head's core 100*b*, wrapped around the head, is 0.187" (5 mm) thick and has a small gap G2. The coil is made of 5000 turns of fine Litz wire and 0.1-ampere current pulses are sent into it by a wearable controller. FIG. 7A shows fringe flux lines 301 injected by the small gap G2 into target T2. FIG. 7B plots a curve 492 showing electric field along the line G2T2. This curve shows that electric field in the scalp at G2 is 100 V/m. Since electric fields below 100V/m are known not to induce pain, this indicates that the wearable stimulator does not cause pain. The field plot 492 also shows that the electric field increases with target depth. In contrast, with prior-art large-gap stimulators the electric field decreases with target depth. Specifically, FIG. 7B shows that the electric field E2 at target nerve T2 is 122 V/m. It is well known that fields stronger than 100 V/m stimulate the nerves; thus, it is evident that the wearable stimulator 100*b* can stimulate deep targets.

Recently, an invasive surgical procedure called deep brain stimulation (DBS) was developed to treat disorders such as Parkinson's disease, Alzheimer's disease etc by stimulating deep targets T2. This procedure pushes two 100 mm long electrode deep into the brain and applies current between the two. It requires risky brain surgery, which can have several side effects. In contrast, the disclosed wearable stimulator can stimulate deep targets without surgical risk. Thus wearable stimulator can be used to stimulate not only shallow targets (depths <30 mm) but also deep targets (depths 30 to 80 mm) without risks. The treatable diseases include hallucinations, drug craving, Obsessive Compulsive Disorder and Attention Deficit Disorder, Parkinson's disease, Alzheimer's disease etc.

Arthritis and Knee Injuries

Figure 8A:
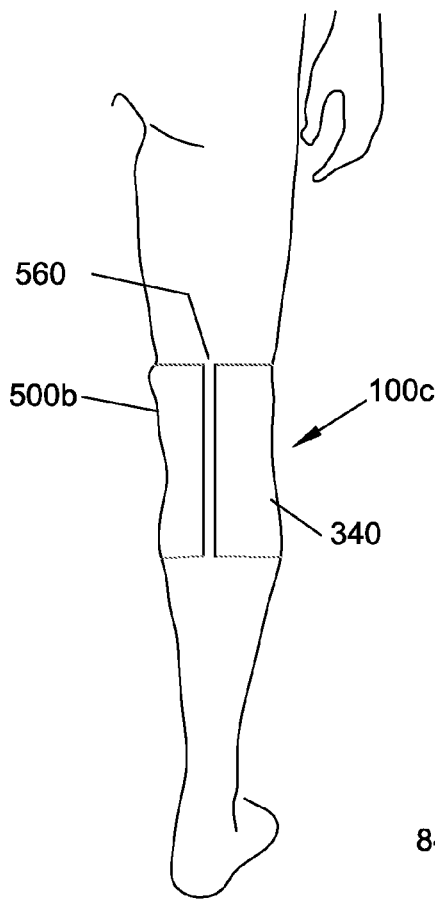
FIG. 8 shows a wearable stimulator to treat osteo-arthritis and knee injuries, with FIG. 8A showing the stimulator head wrapped over the knee and FIG. 8B showing cross-section of the stimulator head healing the ligaments.

Osteo-arthritis is joint pain due to damage of cartilage or bones (around knee joint or cervical spine, hip etc). There seems to be no cure to arthritis, but drugs or physiotherapies are prescribed to reduce severity of pain: drugs have side effects and physiotherapy can cause undue physical strain. In contrast, magnetic stimulation described below does not suffer from either of these ill effects. Normally cartilage cells secrete and maintain collagen fibril matrix in a solution of proteoglycans and water. A malfunction causes a decrease in the proteoglycans concentration resulting in destruction or tear of the collagen. The resulting higher stress concentration is sensed by pain receptors in the bone causing osteoarthritis. Magnetic stimulation can reduce this pain via following mechanism. When pulsed fields are normal to cartilage, they induce currents in its conductive elements. It is well known that such induced currents can start producing proteoglycan, see J van Nguyen, Pulsed Electromagnetic Methods for Treating Osteo-arthritis, Physiotherapy, August 2002, Vol. 88, No. 8, pp. 458-470. Such increase in proteoglycans concentration results in tissue regeneration, growth and healing. FIG. 8A shows the disclosed wearable head 100c wrapped around the affected knee 340 that take advantage of this principle to heal the cartilage. The wearable head 100c comprises a cut-core 500b with a small air gap 560 and a coil winding (not shown). The patient orients the stimulator in such a manner that the fringe flux is normal to the affected cartilage. The rate of healing is controlled by amplitude, frequency and duration of stimulation. Typically stepwise-pulsed fields ranges 10 to 25 gauss, frequency ranges 5 to 12 Hz, over 18 sessions of half hour each, showed significant reduction in pain. In a similar fashion, the wearable stimulator can also be used to reduce pain in other areas such as neck pain, post-polio pain, and diabetic foot pain, fibromyalgia etc.

Figure 8B:
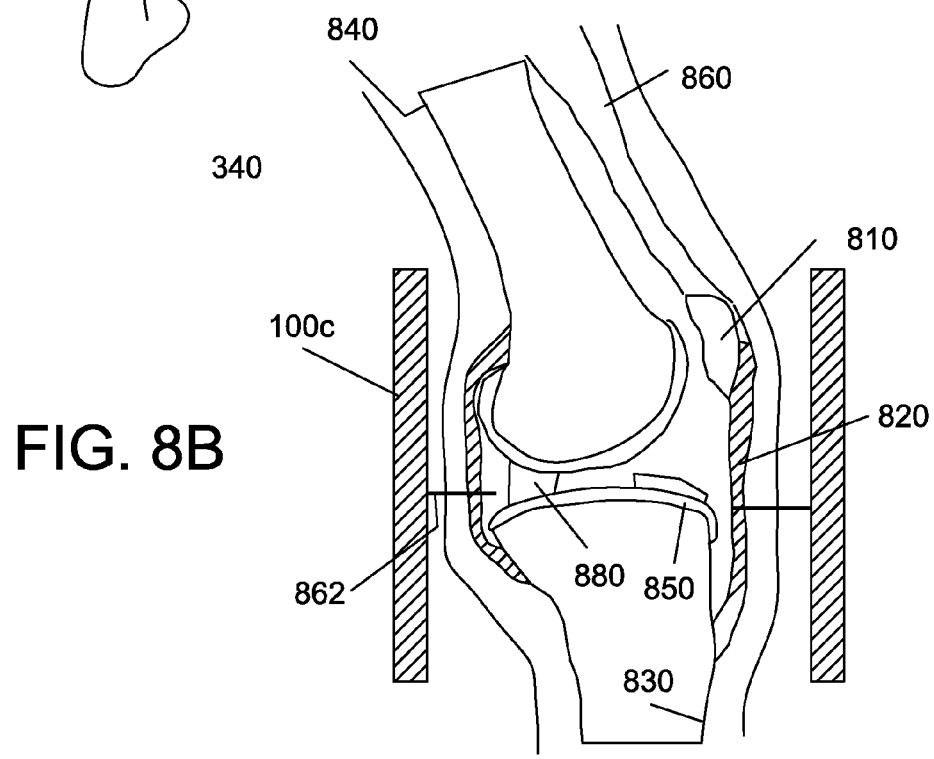

More than 16 million adults in US reportedly limit their activities due to knee related problems. Such disorders include arthritis, muscle disuse atrophy, knee injury etc. Sports require sudden stops, twists and turns and sport-related knee injuries occur when the knee is badly twisted resulting in injury or tearing of the ligaments or muscles in the knees, which in turn get inflamed. The wearable stimulator heals the affected ligaments or muscles in a manner similar to that used to heal cartilage that cause osteo-arthritis. FIG. 8B shows section of the knee joint 340 comprising femur 840, tibia 830 and patella 810, joined by patellar ligament 820 and quadriceps 860. The bone ends are covered by articular cartilage 850 and separated by aterial discus 880. The patient wraps the wearable head around the knee as shown in FIG. 8B. The patient orients the wearable head so that the trapped fringe flux 862 (shown in a plane normal to it) impinges normal to the surface of the damaged muscles or ligaments 820. The thickness of air gap is adjusted so that the applied coil current is just sufficient to start healing the damaged tissue. To start the treatment, the patient downloads an app (specific for the knee injury) into his cell phone controller. He connects the wearable head 100c to the cell phone controller by a cable (not shown). When he initiates the stimulation therapy, the app causes wearable head 100c to radiate magnetic field 862. These fields penetrate the damaged ligament 820 or muscle and induce ionic current pulses in the blood vessels. This causes more blood to flow. The increased blood circulation starts the healing process.

Figure 5A:
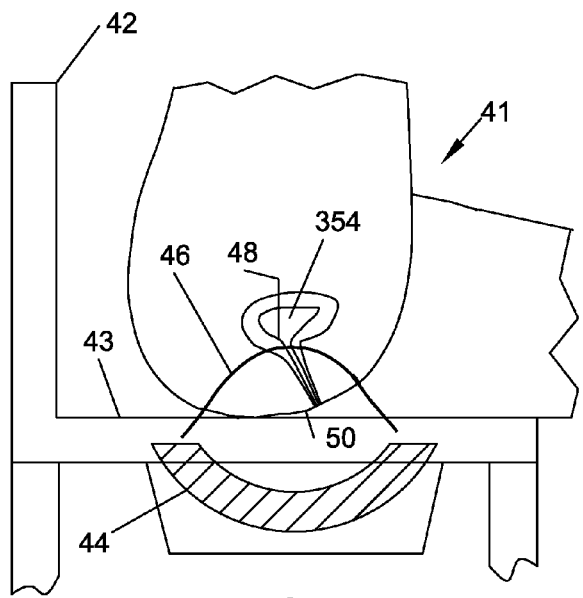
FIG. 5 show prior-art magnetic stimulators that are non-wearable, with FIG. 5A showing a non-wearable stimulator attached to a chair, FIG. 5B showing another non-wearable stimulator close to the knee, FIG. 5C showing another non-wearable stimulator mounted on the wrist and FIG. 5D showing another non-wearable stimulator pressed against neck.
Figure 5B:
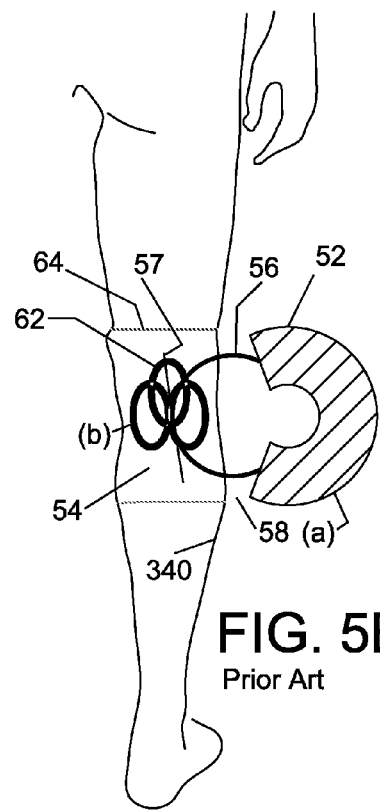
Figure 5C:
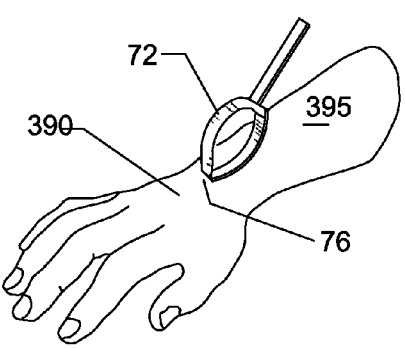
Figure 5D:
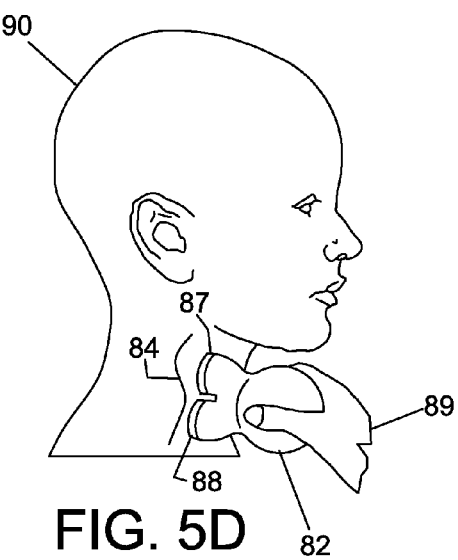

Alternately prior-art used a C-core stimulator as shown in FIG. 5B(a). However, prior-art C-core stimulator is very heavy and held by hand or by fixtures. Holding C-core stimulator ties up the hands so it is not a wearable device. The C-core stimulator also requires several thousands of amperes of current so needs large and heavy pulse generators. Prior art also employed air-cored stimulators shown in FIG. 5B(b) and described in US. Pat. Appln. 20120302821 to treat knee injuries. However, even air-cored stimulators require large currents so are heavy and non-wearable compared to the disclosed wearable stimulator.

Erectile Dysfunction

About 10 million people in US alone are known to suffer from Erectile Dysfunction (ED). In a person without ED, erection starts on sexual arousal in brain, which sends an erection signal through spinal cord down to the erection nerve fibers in the penis. These nerve fibers terminate with nerve endings that inject nitric oxide into the blood. Nitric oxide opens arteries allowing blood to flow into the penile chambers causing erection. Alternatively, in the present disclosure, an ED patient wears the wearable head over the penis like a ring. The wearable head injects the electrical signal into the erection nerves that mimics the erection signal from brain. Thus, the wearable head creates the erection signal instead of the brain to produce erection.

Figure 9A:
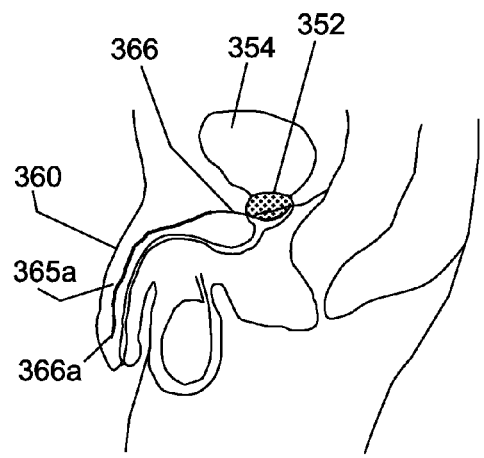
FIG. 9 shows a wearable stimulator to treat erectile dysfunction, with FIG. 9A showing lateral section of a penis, FIG. 9B showing stimulator head injecting fringe flux into erection nerves and FIG. 9C showing the electric field along a line joining air gap and erection nerves.
Figure 9B:
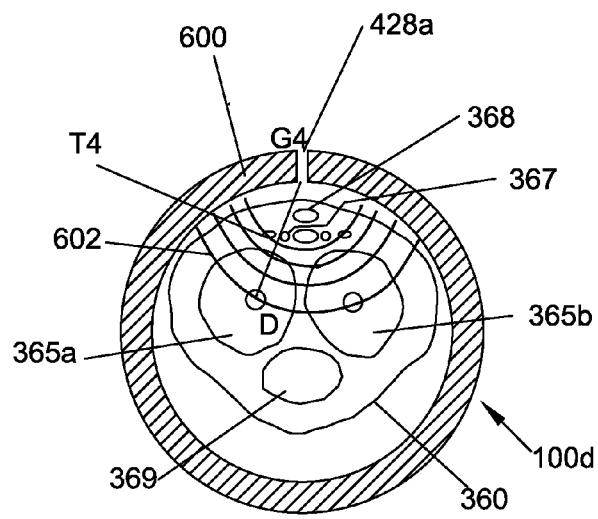

FIG. 9A is a longitudinal section of penis, showing the dorsal nerve (erection nerve) 366. This nerve starts at 366 near the prostate gland 352 (that lies just below the bladder 354) and extends down to point 366a near the tip of the penis 360. The penile cross-section in FIG. 9B shows that the target erection nerve T4 is adjacent to dorsal artery 367 that bring blood into the penis 360. FIG. 9B also shows sponge like penile chambers (corpora cavernosa) 365a, 365b that fill with blood on erection well as the dorsal veins 368 that take out the blood and urethra 369. In a person without ED, on sexual arousal, the brain sends an electrical message through the backbone into the erection nerve T4. These nerve fibers terminate with nerve ending (termed NANC cells) which produce nitric oxide and inject it into the blood. The nitric oxide causes the arteries in the penis 360 to relax. This allows more blood to enter the penile chambers 365a, 365b causing erection.

FIG. 9B shows cross-section of wearable stimulator head 100d around a flaccid penis 360 like a loose ring. The stimulator 100d is a cut-core 600 with a small magnetic gap 428a and a coil (not shown). The inner diameter of the stimulator is larger than an erect penis. The small magnetic gap 428a is vertical and near the apex of the penis 360. The upper portion of the hanging head 100d is close to the penis. He connects the wearable head 100d to a cell phone controller carried in his pockets via a cable (not shown) or a belt-clip. The treatment starts with him downloading an ED-specific software from the internet into the cell phone controller. He then enters the treatment parameters into the ED software. The ED app in the cell phone controller drives the wearable head, which produces fringe flux lines 602. The air gap injects fringe flux lines 602 into the erectile nerve T4. When the injected fringe flux lines are normal to erection nerves, changing fringe flux lines 602 induce maximum potential. A current pulse train then causes an erection message to be generated in the erection nerves. The NANC cells at the nerve endings receive this message and produce nitric oxide. This nitric oxide lets blood from arteries to flow into the penile chambers 365a, 365b thereby causing erection.

Figure 9C:
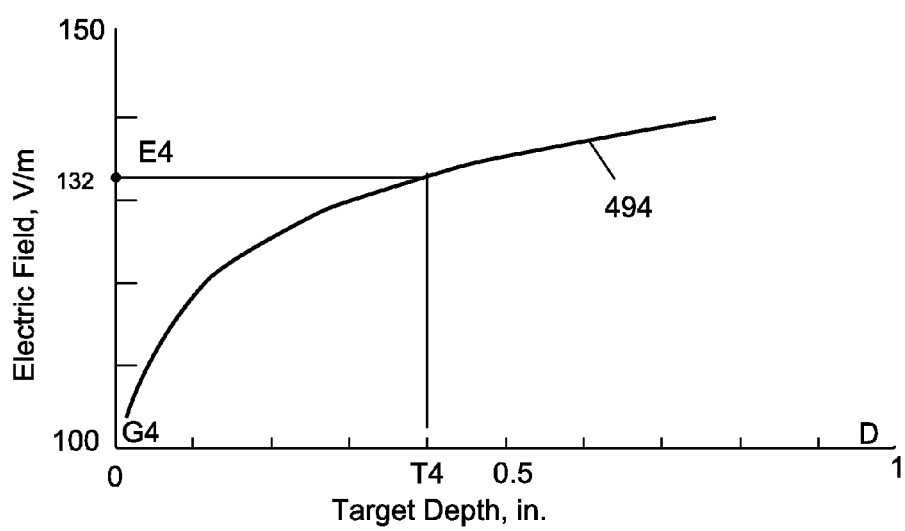

Finite element analysis was conducted to verify that the wearable stimulator 100d needs only minute currents to cause erection. The wearable stimulator 100d is made of a small gapped toroidal core of 45 mm (1.5") inner diameter, 5 mm (0.187") wall. A 5000-turn Litz coil is wound over the core. It is worn around a 20 mm (0.75") flaccid penis. The controller applies a 0.1 amp coil current pulsating at 5000 Hz. FIG. 9B displays the resulting fringe flux lines 602 on the target erection nerves T4. which is at a depth of 10 mm (0.4") from the air gap G4. A 25 mm (1") long line G4D, that starts at air gap G4, passes through the target nerve T4 and ends at the blood vessel D (which is at the center of the penile chamber 365a) is selected to plot variation of electric field. FIG. 9C plots curve 494 for electric field along the line G4D. It shows that electric field E4 at the target erection nerve T4 is about 130 V/m. It is well known that a field above 100 V/m can stimulate nerves. Thus, FIG. 9c indicates that small coil current of 0.1 amp is sufficient to cause erection. This 500 amp turns needed by the disclosed stimulator is nearly two orders of magnitude smaller than the ~15,000 amp turns needed by prior-art stimulators. This results in significant reduction in size and weight of the stimulator and controller compared to those in the prior art, making it wearable.

Incontinence

Figure 10A:
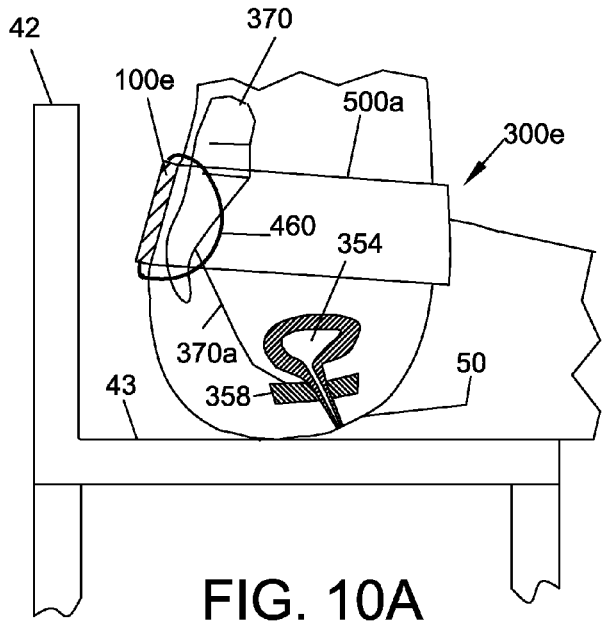
FIG. 10 show a wearable stimulator to treat incontinence, with FIG. 10A showing one embodiment where the stimulator head is worn around the waist, FIG. 10B showing another embodiment with stimulator head worn around tibial nerve in the ankle, FIG. 10C showing a cross-section of ankle with stimulator injecting fringe flux into target tibial nerves and FIG. 10D showing electric field along a line joining small gap and target tibial nerve.

About 10 million people in US reportedly suffer from loss of bladder control, incontinence (both urinal and rectal) and similar disorders. FIG. 10A shows stimulator head 100e worn around the waist, close to the lower spinal cord 370 to treat incontinence. Shown herein is a patient 300e sitting in a chair 42 with her pelvic bottom 50 resting on the base 43 of a chair 42. (The head 100e can be worn in other postures such as standing, walking etc.) The target sacral nerves 370a are located ~25 mm deep from skin in the lower spinal cord 370, just below the bladder 354. The wearable head 100e employs a core 500a that wraps over the waist, with its small gap closest to the sacral nerves. He connects the wearable head 100e to a cell phone controller that is loaded with a stimulation app. The app causes the small gap in the stimulator 100e to inject fringe fields 460 into the sacral nerves 370a. In that process, they penetrate the skin, bones and tissue without causing harm. Changing fields induce voltage in the sacral nerves. This causes ionic currents to flow and pulsating program creates an electrical message. When this message reaches the motor nerve end plates, it causes the bladder muscles 358 to contract and relax. Exercising the muscles 358 by magnetic fields in this fashion builds their strength and endurance and improves blood circulation, thereby treating incontinence.

Figure 10B:
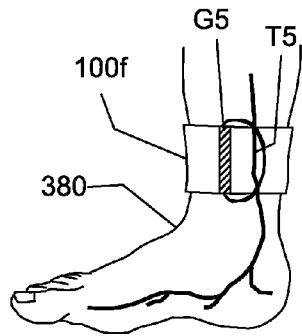
Figure 10C:
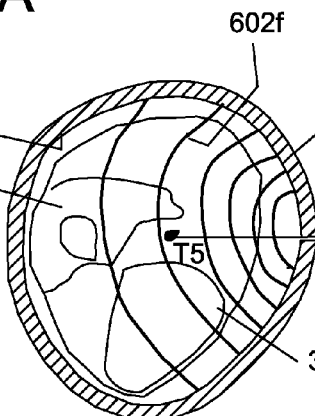

FIG. 10B shows an alternative method that targets tibial nerve T5 in the ankle to treat incontinence. FIG. 10C shows the cross section of the leg, displaying the wearable head 100f around the ankle 380, with its small gap G5 facing tibial nerve T5. The tibial nerve T5 is surrounded by several muscles, such as tibia 342 and fibula 344 and runs down approximately one fingerbreadth posterior of ankle as indicated. The patient orients the wearable head so air gap injects fringe flux 602f into the tibial nerve T5 at right angles as shown. The patient determines the range of current needed by sending a test pulse. He establishes a lower bound by sensing of flexing the big toe and establishes an upper bound of pain threshold as that when he feels discomfort. The stimulation level is normally fixed at 20% to 50% below the pain threshold. Using the wearable head 100f to self-treat in this fashion can greatly reduce cost of treatment. Typical beneficial improvement include the patient experiencing fewer daily urinary voids, fewer daily urge incontinence, fewer urinary voids in the night, increased urinary volumes per void, or improved patient emotional well-being.

Figure 10D:
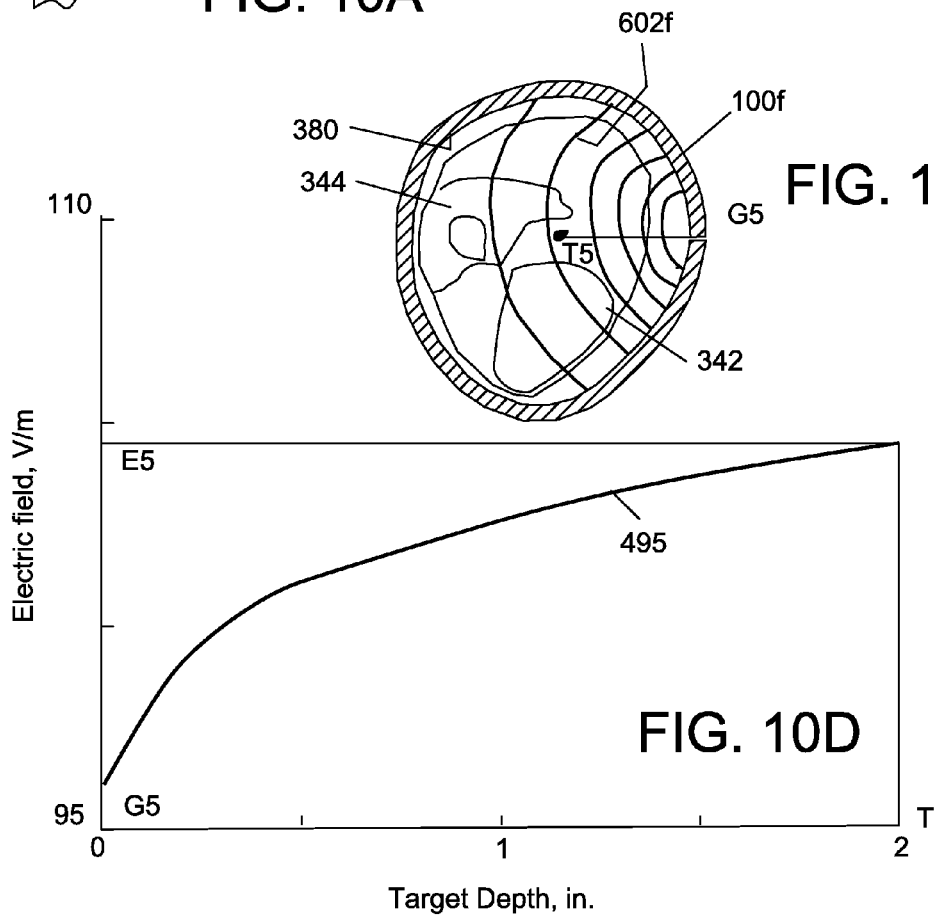

To establish that the wearable stimulator 100f can treat incontinence, finite element analysis was performed on a model of the stimulator surrounding the knee as shown in FIG. 10B, 10C. The goal is to show that only small coil currents are needed to treat incontinence by stimulating the tibial nerve T5. The stimulator 100f is made of a cut-core that surrounds the leg. The diameter of the core is about 4.5" and its wall is 0.25". A 5000 turn Litz coil is wound over the cut-core. The controller applies a 0.05 amp coil current pulsating at 5000 Hz. FIG. 10C displays how the air gap injects fringe flux lines 602f into the target nerves T5 at right angles. A 50 mm (2") long line G5T5 that starts from the air gap G5, and ends with nerve T5, is selected to plot variation of electric field. FIG. 10D plots curve 495 showing the variation of electric field along the line G5T5. It shows that the electric field E5 at target nerve T5 is about 104 V/m. It is well known that a field above 100 V/m can stimulate nerves. Thus FIG. 10D indicates that the wearable stimulator 100f needs only small coil current of about 0.1 amp to stimulate target nerves. This establishes that minute coil currents are sufficient to ionic currents of sufficient strength to stimulate the target nerve T5. This need is nearly one-thousand times smaller than the ~100 amps required by prior-art stimulators. This significant reduction in the coil current requirement allows the disclosed stimulator and controller to be significantly smaller and lighter than those in prior art so makes it wearable.

Wrist Injury

Figure 11A:
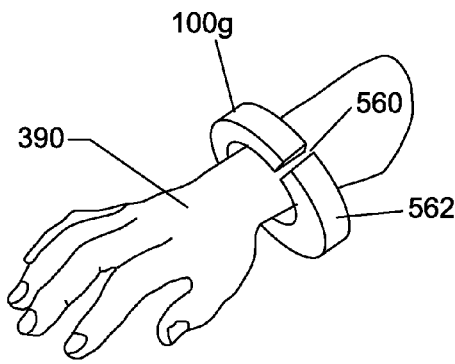
FIG. 11 shows a wearable stimulator to treat wrist injuries, with FIG. 11A showing it wrapped around the wrist, FIG. 11B showing it injecting fringe flux into target nerves and FIG. 11C showing the electric field along line joining the small gap and target nerves.
Figure 11B:
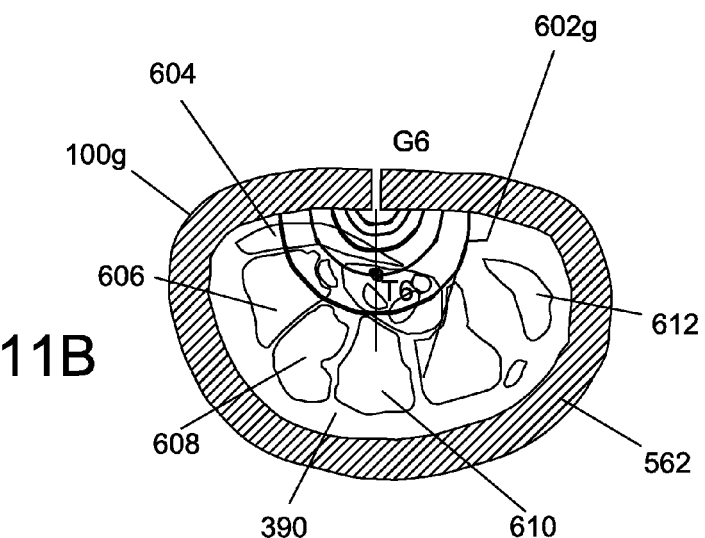

About 0.25 million people in US suffer from wrist injuries due to increased use of computers at workplace resulting in Carpal Tunnel Syndrome, tendonitis, strained wrist etc. FIG. 11A shows a stimulator head 100g worn as a ring over wrist 390 to treat wrist injuries. FIG. 11B shows cross-section of the wrist 390 with a wearable stimulator 100g. Such watch-like ring is comfortable and unobtrusive to wear all day at work, play, or sleep, making it ideal as a nerve sensor or stimulator for long-term measurement in clinical and therapeutic research. The stimulator 100g comprises a cut-core 562 with an air gap G6 and a coil winding (not shown). The air gap lies close to the target medial nerves T6 that affects the carpal syndrome. This nerve T6 lies close to the thumb muscle 604 and greater multang 606, lesser multang 608 and capitlote 610, but far away from the little finger muscles 612. The patient electrically connects the wearable head 100g it to a cell phone controller (not shown). On initiation of treatment, the controller sends pulse currents into the coil of the wearable head 100g. The small gap G6 injects fringe flux lines 602g into the target nerve T6 at right angles, thereby inducing maximum ionic currents. Changing fringe fluxes cause flow of ionic current pulses along the nerves T6, which result in electrical message that cause therapeutic muscular relaxation. The electrical message also improves blood circulation.

Figure 11C:
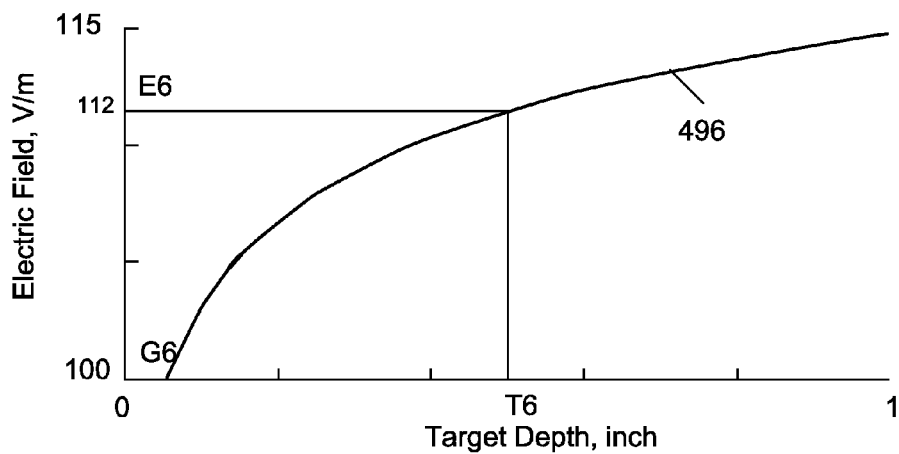

To establish that the wearable stimulator 100g can treat wrist injury, finite element analysis was performed on a stimulator around a wrist. The goal is to show that only minute coil currents are needed to stimulate the target nerves T6. In the model, the stimulator 100g is made of an elliptical cut-core around the wrist. The major and minor axes of the elliptical core are 65 mm×45 mm and its wall is 5 mm. A 4500 turn Litz coil is wound over the cut-core. The controller applies a 0.1 amp coil current pulsating at 5000 Hz. FIG. 11B displays the fringe flux lines 602g across the target nerves T6. A line G6T6 that starts from the air gap G6, passes through target nerve T6 and extends to 1" is selected to plot variation of electric field. The target nerve T6 is at a depth of 12 mm (0.5") from the air gap G6. FIG. 11C plots curve 496 showing the variation of electric field along the line G6T6. It shows that the target nerve T6 sees an electric field E6 of about 112 V/m. It is well known that a field above 100 V/m can stimulate nerves. Thus FIG. 1 IC indicates that the wearable stimulator 100g needs minute coil currents to stimulate target nerves. The needed current is nearly two orders of magnitude smaller than that required by prior-art stimulators. This substantial reduction in the coil current allows the disclosed stimulator and controller to be significantly smaller and lighter than those in prior art so makes it wearable.

The finite element method employed to verity the operating principle relies on Maxwell law, $$\nabla x \frac{1}{\mu}(\nabla xA) = -(\sigma + j\omega\varepsilon)(j\omega A + \nabla\phi)$$

where A is a representation of the flux density B, A≡∇×B. The electric field E≡jωA+∇ϕ where ϕ=voltage potential. Current density J=σE. Charge density $C_d$=J/f. Here σ=conductivity, $\mu=\mu_o\mu_r$=magnetic permeability where $\mu_r$=relative permeability, $\mu_o$=permeability of free space=$4\pi 10^{-7}$ N/A$^2$ and $\in=k\in_o$=permittivity, k=dielectric constant, $\in_o$=permittivity of free space=$8.854\times 10^{-12}$ F/m and ω=angular frequency 2πf, where f=pulse frequency in Hz.

One sizes the wearable head to deliver the electric field that is strong enough to induce action potentials but weak enough not to cause severe pain. Generally, one establishes the minimum stimulating field $E_{min}$ and pain threshold field $E_{max}$ by tests on individual patients. But they can be set as 100 V/m and 200 V/m respectively as per following guidelines. Fields higher than ~100 V/m can stimulate nerves per U.S. Pat. Nos. 7,320,664, 7,824,324, 7,857,746, 7,963,903 and 20110015464 so $E_{min}$ is set to 100V/m. It is well known that ~100V/m electric field cause twitching of thumb but not pain. Pain may be caused by excessive force exerted by ionic currents on the walls of axons. ANSI specifies 200 V/m as the allowable electric field above 10 MHz. Fields above 200 V/m could also cause seizures per U.S. Pat. No. 7,104,947 and Wasserman, E. M., Risk and safety of repetitive transcranial magnetic stimulation suggested guidelines, Electroencephalography and Clinical Neurophysiology, Vol. 109, pp. 1-16, 1998 and Vasques, X et al, A target specific electrode and lead design for internal globus pallidus deep brain stimulation, Stereotactic Functional Neurosurgery, Vol. 88, No. 129-137, 2010. So one sizes the wearable medical device to apply fields that are higher than $E_{min}$~100 V/m to stimulate the target nerves, but lower than the pain threshold $E_{max}$~200 V/m.

Thus, the disclosed wearable stimulator offers several advantages over prior-art non-wearable stimulators. The patient is in full control of every step of therapy. The patient sets the time and place of treatment that is most convenient to him. He sets the treatment duration, strength of pulse, pulse frequency, strength etc that is optimal for his specific disorder. The therapy can be used in arbitrarily different environments. With a wearable stimulator a patient can treat himself in the privacy of home, without supervision of a doctor. For severe or more complicated illnesses, the patient can still seek the service of trained medical professionals who can provide additional guidance and specialized support. Or he can stop the treatment at any time by clicking a "Stop Treatment" icon. In essence, the patient can treat himself thereby saving significant costs.

The wearable stimulator head is operated hands-free, which allows the patient to carry on with his daily routine uninhibited. The patient can wear it in a sitting, standing or walking position. The wearable head operates with minute currents, and does not need heavy non-wearable pulse generators. Because currents are relatively low, the wearable head does not overheat. As a result, it does not cause skin burn even though it is in contact with head. Since the wearable head dissipates less waste heat, it does not require complex cooling system.

In the present disclosure, the skin nerves see lower electric field than those near the target cells. As the fringe flux moves away from gap, it encloses more turns, so the electric field becomes stronger. The electric field due to fringe flux increases as one move from skin to target nerves. Thus since the wearable head applies smaller electric field to nerves in the skin, so it does not cause pain. In contrast, in prior-art, the nerves within skin see significantly larger fields than those seen by the target nerves. As a result, they can be overstimulated leading to severe pain.

The controller in accordance to the present disclosure is wearable. The magnetic gap in the present disclosure is less than 0.03 inch (1 mm): that in prior art is greater than 4 inch (100 mm), so is two orders of magnitude higher. The reluctance of the small magnetic gap is two orders of magnitude lower than conventional large magnetic gap. Thus, the electric current required by the small-gap stimulator is two to three orders of magnitude smaller than that required by large-gap stimulators. Such drastically smaller current allows even ordinary cell phones to be used as wearable stimulator controllers. Low current also greatly reduces heat dissipation so reduces temperature rise, preventing body injury and discomfort and the stimulator does not need custom cooling equipment. It also does not need large rest periods during treatment to cool the stimulation head. In contrast, prior art controllers need large currents and are heavy and nonwearable.

Thus, the wearable magnetic stimulator offers unsurpassed flexibility and convenience to treat a variety of diseases. The small size, lightweight and absence of excessive heat make wearable magnetic stimulator a patient-friendly medical device. The wearable magnetic stimulator offers very small footprint. It uses few parts and is economical to manufacture. Its lower currents produce low eddy loss and hence has lower temperature rise, which allows it to be cooled by natural convection. It can be used to treat a wide range of disorders controlled by nerves close to the skin.

Even though the wearable magnetic stimulator is illustrated to treat few example disorders, it can be equally effective to cure many other disorders. For example, to treat some allergies, the patient can wear the stimulator head over temples or forehead. For treating arthrosis, one can wear it over the knee or lower portion of spine. For treating asthma, one can wear it over the chest. For improving blood circulation in the feet, wearing the stimulator over the sole of the feet is optimal. For treating laryngitis, wearing it over upper chest or throat is suggested. For curing bronchitis infection, wearing it over upper chest or sternum is beneficial. To treat other disorders, the patient and his doctor can locate a specific peripheral nerve that controls the disorder and secure the wearable head close to it.

A person skilled in the art, having the benefit of the teachings of this specification, may affect numerous modifications thereto without departing from the scope and spirit of the invention. The requirements, data and features of the wearable magnetic stimulator are described herein merely to provide examples of various aspects of the present invention; the invention is not limited to these examples.

What is claimed:

1. A medical device comprising a looped, continuous magnetic core with a coil winding, the looped, continuous magnetic core comprising first and second ends forming a small gap of 0.004 to 0.020 inches therebetween, the first and second ends are wrappable around a limb of a human containing a nerve fiber, wherein:
   (a) the looped, continuous magnetic core radiates a fringe flux that emanates from the first end of the small gap and is received by the second end of the small gap, and
   (b) the fringe flux intercepts the nerve fiber.

2. A magnetic stimulator for treating disorders of a patient comprising:
(a) the medical device in claim 1,
(b) a controller comprising a power source, a computer with treatment software that causes the computer to output a pulsed signal, said controller being adapted to be in a clothing of a patient,
(c) a cable that electrically connects the controller with the medical device.

3. A medical device in claim 1 that generates an electric field of at least 100 V/m in the nerve fiber.

4. A medical device in claim 1 generating an electric field of at least 100 V/m in nerve fibers located at depths of up to 80 mm below a skin of a patient.

5. A medical device in claim 1 wrappable around a neck to treat depression, epilepsy or migraine headache, wherein a line joining the small gap and a nerve fiber inside the neck is normal to the small gap.

6. A medical device in claim 1 wrappable around a scalp to treat depression, Parkinson's disease or Alzheimer's disease, wherein a line joining the small gap and a nerve fiber inside the brain is normal to the small gap.

7. A medical device in claim 1 wrappable around a kneecap to treat knee injuries and osteoarthritis, wherein a line joining the small gap and a nerve fiber inside the kneecap is normal to the small gap.

8. A medical device in claim 1 wrappable over a penis to treat erectile dysfunction, wherein the small gap is at an apex of the penis.

9. A medical device in claim 1 wrappable over an ankle to treat incontinence, wherein the small gap injects a fringe flux normal to a nerve fiber inside the ankle.

10. A medical device in claim 1 wearable over a wrist to treat carpal tunnel syndrome, wherein a fringe flux line is normal to a nerve fiber inside the wrist.

11. A looped, continuous magnetic core comprising two segmented cores, each core segment including a first and second end, wherein the first ends of each core segment are butt-joined and the second ends of each core segment are separated by a small gap of 0.004 to 0.020 inches therebetween, wherein the second ends are wrappable around a limb of a human containing a nerve fiber.

* * * * *